United States Patent [19]

Zappacosta

[11] Patent Number: 5,141,499
[45] Date of Patent: Aug. 25, 1992

[54] PERITONEAL DIALYSIS CATHETER

[76] Inventor: Anthony R. Zappacosta, 624 Manor Rd., Narberth, Pa. 19042

[21] Appl. No.: 773,403

[22] Filed: Oct. 9, 1991

[51] Int. Cl.$^5$ ............................................. A61M 5/00
[52] U.S. Cl. ..................................... 604/175; 604/280
[58] Field of Search ................... 604/175, 29, 264, 280

[56] References Cited

U.S. PATENT DOCUMENTS

| | | | |
|---|---|---|---|
| 3,633,585 | 1/1972 | McDonald, Jr. | 128/348 |
| 3,638,649 | 2/1972 | Ersek | 604/175 |
| 4,184,497 | 1/1980 | Kolff et al. | 131/213 A |
| 4,278,092 | 7/1981 | Borsanyi et al. | 128/348 |
| 4,279,252 | 7/1981 | Martin | 128/349 R |
| 4,368,737 | 1/1983 | Ash | 604/175 |
| 4,392,855 | 7/1983 | Oreopoulos et al. | 604/175 |
| 4,400,169 | 8/1983 | Stephen | 604/175 |
| 4,490,137 | 12/1984 | Murkheibir | 604/175 |
| 4,676,782 | 6/1987 | Yamamoto et al. | 604/175 |
| 4,681,570 | 7/1987 | Dalton | 604/282 |
| 4,687,471 | 8/1987 | Twardowski et al. | 604/175 |
| 4,772,269 | 9/1988 | Twardowski et al. | 604/175 |
| 4,886,502 | 12/1989 | Poirier et al. | 604/175 |
| 4,935,004 | 7/1990 | Cruz | 604/29 |

OTHER PUBLICATIONS

H. Tenckhoff, et al. "A Bacteriologically Safe Peritoneal Access Device," Trans. Amer. Soc. Artif. Int. Organs, 181-187 (1968).

Primary Examiner—Paul J. Hirsch
Attorney, Agent, or Firm—Woodcock Washburn Kurtz Mackiewicz & Norris

[57] ABSTRACT

According to the present invention, there is provided a novel peritoneal dialysis catheter which comprises a flexible catheter tube having a proximal and a distal end portion. The distal end portion defines flow port means for fluid communication between the bore of the catheter tube and the peritoneal cavity. The catheter carries one to two porous cuff means to facilitate permanent securance of the catheter to the abdominal wall. The improvement of the invention comprises flexible catheter tubing having an internal diameter in the range from about 2.5 to about 5.0 millimeters; and a transcutaneous section which is at least one-half the exterior diameter and at least one half the interior diameter of the flexible catheter tube.

12 Claims, 1 Drawing Sheet

PERITONEAL DIALYSIS CATHETER

FIELD OF THE INVENTION

This invention relates to the field of peritoneal dialysis catheters. More particularly, the invention relates to a peritoneal dialysis catheter having a transcutaneous section and/or a transperitoneal section which is at least one-half the exterior diameter and at least one half the interior diameter of the flexible peritoneal dialysis catheter tube.

BACKGROUND OF THE INVENTION

In the treatment of various diseases, percutaneous access to the peritoneal cavity is necessary. An example is peritoneal dialysis which is often indicated for acute or chronic renal failure. To effect dialysis through the peritoneal cavity, a percutaneous passage is surgically formed through the cutaneous and subcutaneous tissues, rectus muscle and through the peritoneum itself. This passage permits insertion and implantation of a distal portion of the catheter within the peritoneal cavity. A separate caudally directed tunnel is then formed through the subcutaneous and cutaneous tissues with a tunnel exit site in the supra pubic region of the external abdominal wall. A proximal portion of the catheter is inserted into the tunnel thereby maintaining an end of the proximal portion in a downward direction along the abdominal wall. Examples of catheters used in peritoneal dialysis include those disclosed in U.S. Pat. Nos. 3,633,585; 4,184,497; 4,278,092; 4,279,252; 4,368,737; 4,392,855; 4,681,570; 4,687,471; 4,772,269; and 4,935,004.

One example of peritoneal dialysis catheters, the Tenckhoff catheter is commercially available and widely used with patients who must undergo chronic peritoneal dialysis for maintenance in the absence of normal kidney function. The catheter is made of silicone rubber, and has a pair of porous tissue attachment cuffs in spaced relation to each other, so that after implantation of the catheter into the abdominal wall, tissue grows into pores of the cuffs, for secure and permanent anchoring of the catheter in place. Tenckhoff et al., "A Bacteriologically Safe Peritoneal Access Device", Trans. Am. Soc. Artif. Intern. Organs 14:181-187 (1968).

A significant problem with peritoneal dialysis catheters is the risk of post-operative infection, typically infection of the tunnel exit site. The prior art has attempted to address the problem of infection by the use of "swan neck" catheters which are disclosed in U.S. Pat. No. 4,687,471 and 4,772,269 ('471 and '269).

Not withstanding the suggestions of '471 and '269, there remains a need for peritoneal dialysis catheters which reduce the risk of tunnel exit site infection.

SUMMARY OF THE INVENTION

According to the present invention, there is provided a novel peritoneal dialysis catheter which comprises a flexible catheter tube having a proximal and a distal end portion. The distal end portion defines flow port means for fluid communication between the bore of the catheter tube and the peritoneal cavity. The catheter carries one to two porous cuff means to facilitate permanent securance of the catheter to the abdominal wall. The improvement of the invention comprises flexible catheter tubing having an internal diameter in the range from about 2.5 to about 5.0 millimeters; and a transcutaneous section and/or a transperitoneal section which is at least one-half the exterior diameter and at least one half the interior diameter of the flexible catheter tube.

The smaller exit site, transcutaneous and/or transperitoneal, is believed to improve the cosmetic effect with consequent better patient acceptance especially in the pediatric continuous ambulatory peritoneal dialysis (CAPD) population. Further, it is believed the smaller exit site(s) will result in a reduction in the incidence exit site-tunnel infection.

DETAILED DESCRIPTION OF THE INVENTION

In this invention, a peritoneal catheter comprises a flexible catheter tube, which may be made of silicone rubber or equivalent material. The tube may be of the "swan neck" type as disclosed and claimed in U.S. Pat. Nos. '471 and '269 described above. The tube has a proximal and distal end portion. The distal end portion defines flow port means for fluid communication between the bore of the catheter tube and the peritoneal cavity. The catheter also carries porous cuff means to facilitate permanent securance of the catheter to the abdominal wall.

The porous cuff means on the catheter may be any cuff used for tissue attachment to a catheter. While a single, porous cuff may be used, it is preferable to use a pair of spaced, porous cuffs in the manner of the well-known Tenckhoff catheter as it is currently commercially available. The cuff may be made from a woven biocompatible material known in the art, such as Dacron ® or Tecoflex ®.

Figure 1:
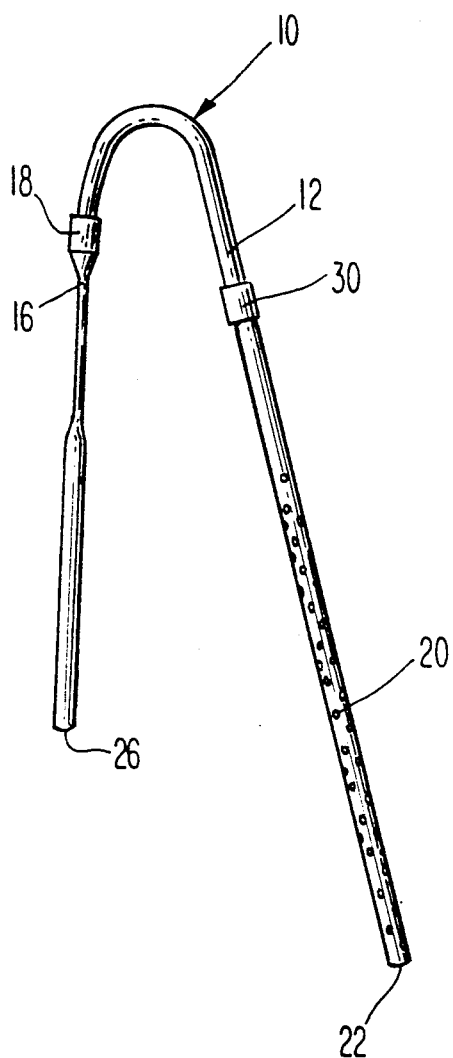
FIG. 1 is a plan view of one embodiment of the catheter of this invention.
Figure 2:
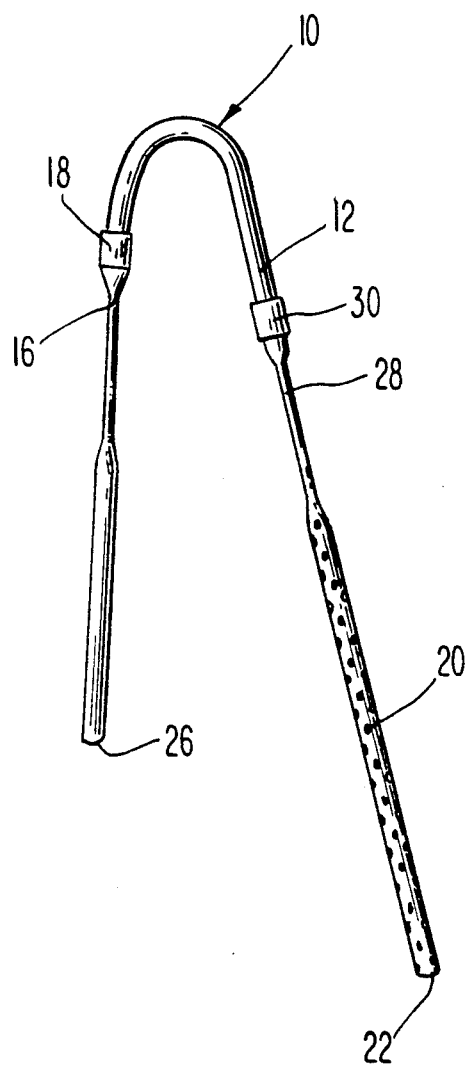
FIG. 2 is a plan view of one embodiment of the catheter of this invention.

Referring now to the drawings, the numeral 10 generally designates a peritoneal catheter of the design of a commercially available Tenckhoff catheter, except as otherwise described herein. The catheter 10 comprises flexible catheter tubing 12 which may be made of silicone rubber or other appropriate material. Flexible catheter tubing 12 refers to the entire catheter with the exception of the transcutaneous section 16 as shown in FIGS. 1 and 2 and the transperitoneal section 28 as shown in FIG. 2. However, the transcutaneous section 16 and the transperitoneal section 28 are also made of flexible catheter tubing which can be the same or different as the flexible catheter tubing 12.

Adjacent the distal end of the catheter 22, a plurality of flow ports 20 are formed in the wall of the catheter. The distal end 22 of the catheter may be open as well for additional flow communication between the exterior and the bore of the catheter.

The proximal end 26 defines an open bore as well for receiving an adaptor of known design, typically titanium, to provide connection with a transfer set or other means for flow communication with peritoneal dialysis solution containers.

A pair of cuffs 18, 30 of known design are also provided. Outer cuff 18 is intended to be positioned within the abdominal wall tunnel about 2 cm from the outer skin, while cuff 30 is positioned adjacent the inner end of the abdominal tunnel.

In accordance with this invention as shown in FIGS. 1 and 2, the transcutaneous section 16 of the catheter 10 is at least one half the exterior diameter and at least one half the interior diameter of flexible catheter tubing 12. The transcutaneous section 16, refers to the section of the catheter that crosses the skin of the patient. The dimensions of the catheter 10 may vary considerably depending on the size of the patient and other factors but, in general, the length of the catheter 10 would normally fall within the range of about 25 to 100 centimeters. The exterior diameter of flexible catheter tubing 12 is within the range of about 4.5 to about 7 millimeters, preferably about 5 millimeters. The interior diameter is within the range of about 2.5 to about 5 millimeters and preferably about 3 millimeters. Thus, the flexible catheter tube 12 generally has a larger internal diameter than a standard Tenckhoff catheter so that an acceptable flow rate is achieved through the catheter 10 which includes the ultra thin-walled transcutaneous and/or transperitoneal sections 16 and 28.

To reduce exit site infection and to improve cosmetic effects, in accordance with this invention, the exterior diameter and interior diameter of the transcutaneous catheter section 16 are at least one half that of the flexible catheter tubing 12. Conveniently, the exterior diameter and interior diameter of the transcutaneous section of the catheter is about 2.3 mm and about 1.3 mm respectively.

In another embodiment of the invention as shown in FIG. 2, the transperitoneal section 28 of the catheter may be reduced in exterior and interior diameter as described above for the transcutaneous section 16. The transperitoneal section 28 refers to the section of the catheter that crosses the peritoneum. Conveniently, the length of the transcutaneous 16 and the transperitoneal section 28 of the catheter is that amount which is necessary to cross the skin and/or the peritoneum of the patient and is generally about 2.5 centimeters to about 7.5 centimeters. The transcutaneous section 16 can of course extend to the proximal end 26 of the catheter 10. Conveniently, the proximal end can be as depicted in the figures so as to be compatible with standard connections.

Regarding the transcutaneous and transperitoneal sections of the catheter of this invention, the narrower tubing may be continuous to the connection with the flexible catheter tube 12. Alternatively, the joinder of the narrow and larger tubes may be conveniently accomplished by melting the ends together taking care not to occlude the internal space within the catheter tube.

EXAMPLE

Materials and Methods

The catheter used in this Example has a 9 French 8 centimeter transcutaneous section which extends from the subcutaneous cuff (just under the placement site) to the transfer set adapter. The external diameter of this tunnelexit site section is 2.3 millimeters and the internal diameter is 1.3 millimeters, compared to the standard 15 French Tenckhoff which has an internal diameter of 2.6 millimeters and an external diameter of 5.0 millimeters. The intraperitoneal section of the catheter of this invention is 15 French but the internal diameter is 3 millimeters. FIG. 1 shows the catheter exit site. A short segment of standard Tenckhoff is bonded pending availability of a 9 French adapter that fits current transfer sets. Ten of these catheters were placed in ten patients ages forty-three to eighty-seven, seven by the Seldinger technique (Zappacosta et al., *J Am Soc Artif Int Organ*, 37:13-15 (1991)) and three by surgical placement.

The time for outflow of 2,000 cc in over five hundred exchanges among ten patients was seven to twenty minutes. Inflow time was unchanged from standard Tenckhoffs. There were no exit site-tunnel infections in 365 patient days (median 29 days, mean 36). Fibrin was noted to pass easily through the 9 French section, and there were no instances of poor drainage that could be attributed unequivocally to fibrin obstruction in the 9 French section.

Discussion

This ultra thin-walled catheter section demonstrated durability over 12 patient months. The smaller exit site is believed to improve the cosmetic effect with consequent better patient acceptance especially in the pediatric CAPD population. It is believed the smaller exit site will result in a reduction in the incidence exit site-tunnel infection. It is clear that there is no need to have a 15 French Tenckhoff catheter tunnel exit site and the catheter of this invention functioned without any reduction of the dialysate flow rates.

I claim:

1. A peritoneal catheter which comprises a flexible catheter tube having a proximal and a distal end portion, said distal end portion defining flow port means for fluid communication between the bore of the catheter tube and the peritoneal cavity, said catheter carrying one to two porous cuff means to facilitate permanent securance of the catheter to the abdominal wall, the improvement comprising:
   said flexible catheter tubing having an internal diameter in the range from about 2.5 to about 5.0 millimeters; and
   a transcutaneous section which is at least onehalf the exterior diameter and at least one half the interior diameter of the flexible catheter tube.

2. The catheter according to claim further comprising:
   a transperitoneal section which is at least one-half the exterior diameter and at least one half the interior diameter of the flexible catheter tube.

3. The catheter according to claim 1 wherein the flexible catheter tube has an exterior diameter of about 4.5 to about 7 millimeters.

4. The catheter according to claim 1 wherein the flexible catheter tube has an external diameter of about 5.0 millimeters and an internal diameter of about 3.0 millimeters.

5. The catheter according to claim 1 wherein the transcutaneous section has an exterior diameter of about 2.5 to about 3.5 millimeters and an interior diameter of about 1.25 to about 2.5 millimeters.

6. The catheter according to claim 1 wherein the transcutaneous section has an exterior diameter of about 2.3 millimeters and an interior diameter of about 1.3 millimeters.

7. The catheter according to claim 1 wherein the transcutaneous section is about 2.5 centimeters to about 7.5 centimeters in length.

8. The catheter according to claim 2 wherein the flexible catheter tube has an exterior diameter of about 4.5 to about 7 millimeters.

9. The catheter according to claim 2 wherein the flexible catheter tube has an external diameter of about 5.0 millimeters and an internal diameter of about 3.0 millimeters.

10. The catheter according to claim 2 wherein the transperitoneal section and the transcutaneous section have an exterior diameter of about 2.25 to about 3.5 millimeters and an interior diameter of about 1.25 to about 2.5 millimeters.

11. The catheter according to claim 2 wherein the transperitoneal section has an exterior diameter of about 2.3 millimeters and an interior diameter of about 1.3 millimeters.

12. The catheter according to claim 2 wherein the transperitoneal section is about 2.5 centimeters to about 7.5 centimeters in length.

* * * * *

UNITED STATES PATENT AND TRADEMARK OFFICE
CERTIFICATE OF CORRECTION

PATENT NO. : 5,141,499
DATED : August 25,1992
INVENTOR(S) : Zappacosta

It is certified that error appears in the above-identified patent and that said Letters Patent is hereby corrected as shown below:

Column 1, Line 31 delete "4,278.092;" and insert therefor --4,278,092;--.

Column 4, Line 1 delete "Organ," and insert therefore --Organs--.

Column 4, Line 37 delete "onehalf" and insert therefor --one half--.

Column 4, Line 40 delete "claim further" and insert therefor --claim 1 further--.

Column 4, Line 42, "one-half" and insert therefor --one half--."

Signed and Sealed this

Ninth Day of November, 1993

Attest:

BRUCE LEHMAN

Attesting Officer

Commissioner of Patents and Trademarks